(12) United States Patent
Nafziger

(10) Patent No.: US 6,336,458 B1
(45) Date of Patent: Jan. 8, 2002

(54) PROTECTIVE SHIELD FOR PATIENTS USING HICKMAN-STYLE CATHETERS OR OTHER MEDICALLY IMPLANTED DEVICES

(76) Inventor: Douglas A. Nafziger, 2645 Castleton Ave., Toledo, OH (US) 43613

( * ) Notice: Subject to any disclaimer, the term of this patent is extended or adjusted under 35 U.S.C. 154(b) by 0 days.

(21) Appl. No.: 09/545,800

(22) Filed: Apr. 8, 2000

(51) Int. Cl.[7] .................................................. A61F 13/00
(52) U.S. Cl. ........................ 128/846; 128/875; 604/179
(58) Field of Search ................................ 128/846, 869, 128/874, 875; 604/179; 2/102; 602/19

(56) References Cited

U.S. PATENT DOCUMENTS

| | | | | |
|---|---|---|---|---|
| 4,438,763 A | * | 3/1984 | Zablen | 604/179 |
| 4,474,859 A | * | 10/1984 | Steiger | 434/268 |
| 4,709,695 A | | 12/1987 | Kohn et al. | 128/858 |
| 4,926,883 A | | 5/1990 | Strock | 128/888 |
| 4,989,265 A | | 2/1991 | Nipper et al. | 2/462 |
| 5,248,293 A | * | 9/1993 | Hubbard | 128/875 |
| 6,032,289 A | * | 3/2000 | Villapiano | 2/102 |

* cited by examiner

*Primary Examiner*—Michael A. Brown

(57) ABSTRACT

A protective chest shield device having medical applications is disclosed. The chest shield is designed to prevent damage to patients wearing an indwelling catheter or other medically implanted device during participation in athletic activities. The device consists of a rigid shield below which padding is placed at appropriate locations as to create a void so as to prevent contact with the external or internal components of the medical device. It is affixed to the patient by means of an adjustable harness.

1 Claim, 4 Drawing Sheets

PROTECTIVE SHIELD FOR PATIENTS USING HICKMAN-STYLE CATHETERS OR OTHER MEDICALLY IMPLANTED DEVICES

CROSS-REFERENCE TO RELATED APPLICATIONS

Not applicable.

BACKGROUND OF THE INVENTION

The present invention relates to a shield that protects the patient's site of a Hickman-style catheter, or other indwelling catheter, or other medical device, from damage.

Hickman catheters, otherwise known as, but not limited to, a Broviac, a Hohn's, a multi-lumen central venous line, are surgically implanted into a patient's chest, connecting to a vein or artery. The purpose of the catheter is to deliver medications such as chemotherapy drugs and to draw blood samples for testing on patients undergoing long term medical treatment regimens. The site at which the catheter is implanted through the patient's skin, as well as the subcutaneous area where the catheter attaches to a blood vessel, must be protected from impact in order to protect the integrity of the catheter and the patient from an injury that may require surgery.

Several types of chest protectors have been developed. U.S. Pat. No. 4,989,265 to Nipper and Ettinger (1991) discloses a device that protects the chest, ribs, and shoulders of the wearer from impact by using padding and a convoluted surface. This device, however, does not prevent contact with the site of an indwelling catheter or other medically implanted device. U.S. Pat. No. 4,926,883 to Strock (1990) also shows a device that protects the wearer from impact. Although more flexible, it too does not prevent contact with the site of an indwelling catheter or other medically implanted device.

U.S. Pat. No. 4,709,695 to Kohn and Shields (1987) describes a medical protective device that is coupled to patient by means of an adhesive or Velcro™. Although the device protects a medical site, it is not intended to withstand the impact of vigorous activity. In addition, because of regular care required with an indwelling catheter, additional adhesives are undesirable.

Efforts have been made in the past to secure a catheter that is susceptible to being accidentally displaced or even pulled completely from the body. This protective shield differs significantly from existing protective devices, such as many chest protectors, in that the padding surrounds the catheter site, beneath the plastic shield, creating a void in order to maintain space between the protective shield and the body with the components of the catheter itself.

The invention entitled Protective Shield For Patients Using Hickman-Style Catheters or Other Medically Implanted Devices allows the patient the ability to participate in sports and activities that may impact the above mentioned body region. These activities include, but are not limited to, such sports as soccer, tennis, baseball, kickball, lacrosse, karate, basketball, fencing, volleyball, and many general physical education program activities. An unprotected catheter site placed under heavy impact may cause severe discomfort, tissue damage, possible infection, and the need for surgical replacement. This is the first device that will prevent injury to the patient and to allow a patient wearing a catheter to comfortably participate in physical activity.

SUMMARY

In accordance with the present invention of an article that protects patients with a medically implanted device comprising a rigid shield, impact absorbing material, and an adjustable harness.

OBJECTS AND ADVANTAGES

Accordingly, besides the objects and advantages of the shield described in my above patent, several objects and advantages of the present invention are:

(a) to protect the site of an indwelling catheter or other medically implanted device;

(b) to allow the patient to continue, or pursue, rigorous activities without fear of site damage;

(c) to provide for an adjustable fit;

(d) to be reusable; and (e) to be available in different sizes.

Further objects and advantages are to provide a protective shield which can maintain, or improve, the quality of life to patients with an indwelling catheter or other medically implanted device. Still further objects and advantages will become apparent from the ensuing description and drawings.

DRAWING FIGURES

REFERENCE NUMERALS IN DRAWING

| | |
|---|---|
| 10 frontal site shield | 12 backing material |
| 14 pad - left | 16 pad - right |
| 18 pad - center | 20 enclosure - hook |
| 22 enclosure - loop | 24 felt-like material |
| 26 catheter | |

DESCRIPTION OF INVENTION

Figure 1:
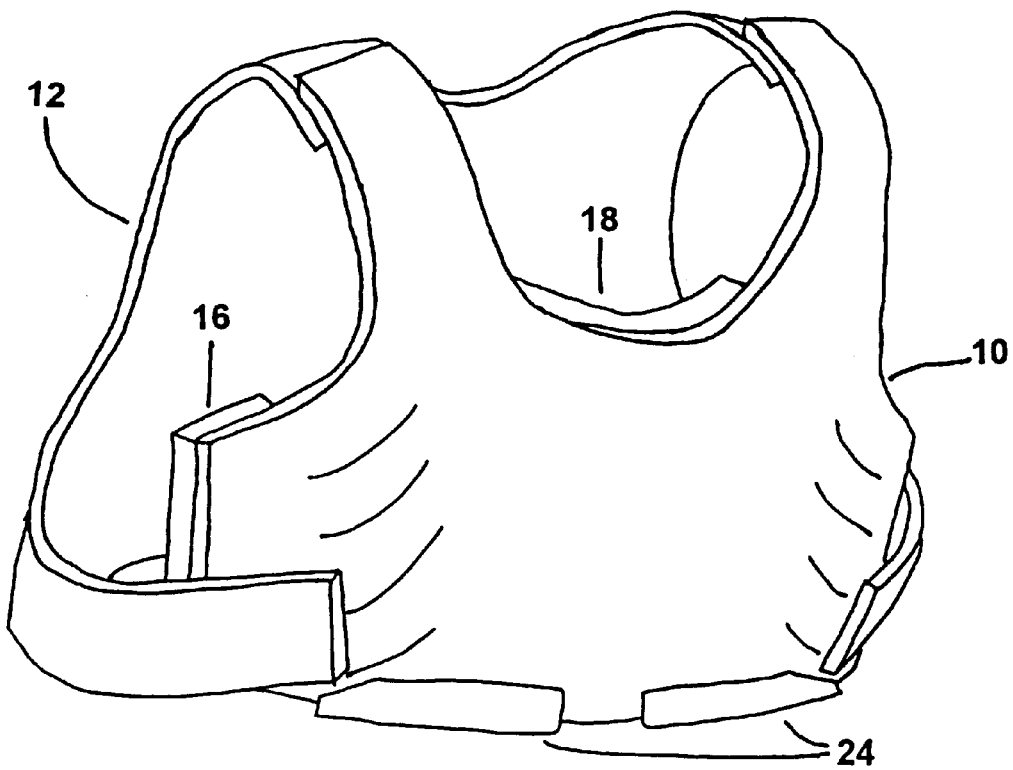
FIG. 1 shows a top-angled view of the assembled device.
Figure 2:
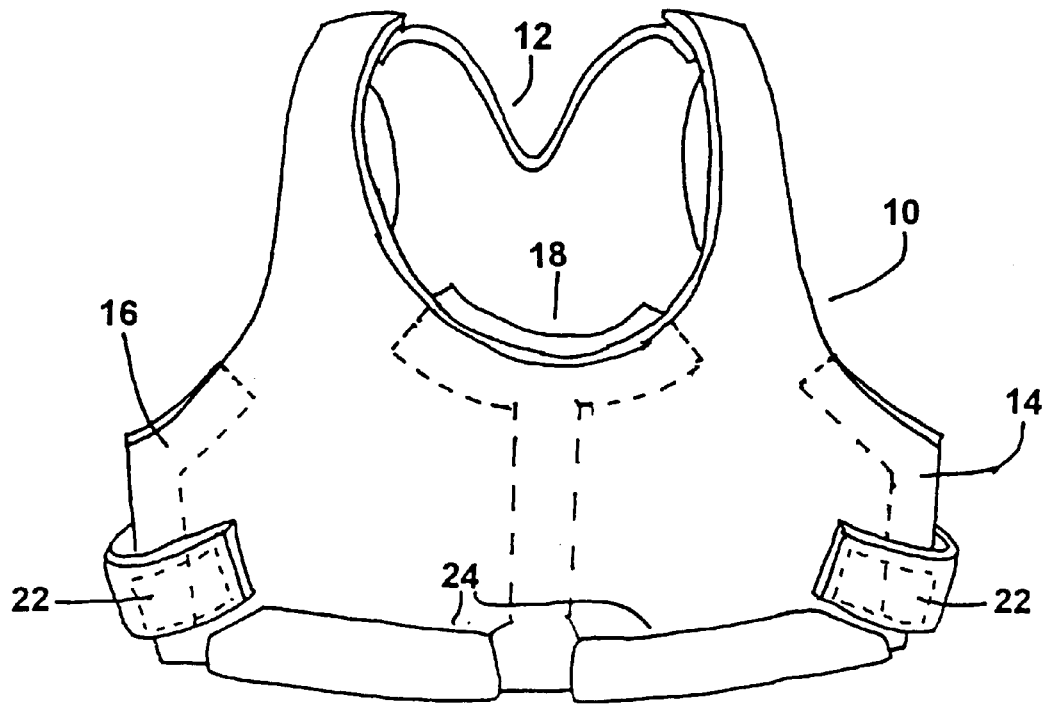
FIG. 2 shows a front view of the assembled device.
Figure 3:
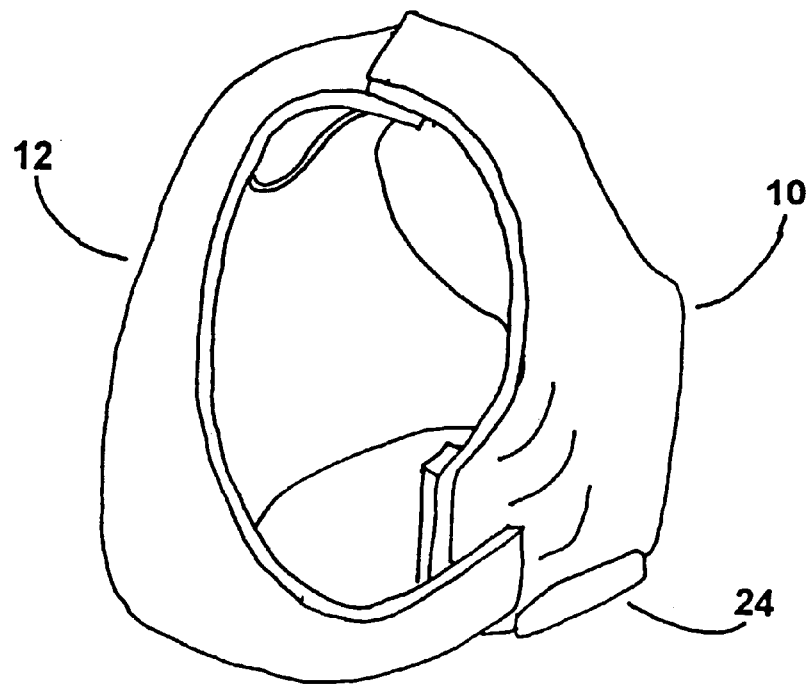
FIG. 3 shows a side view of the assembled device.

The device shown in FIGS. 1–3 shows a frontal site shield 10 that is shaped to fit a patient's upper torso. The frontal site shield 10 is made from a rigid plastic material that holds its shape in order to somewhat snugly fit to the torso and also to withstand impact during athletic or other physical activities. A felt material 24 is placed on the lower edges of the frontal site shield 10 in order to eliminate abrasion of catheter 26.

Figure 4:
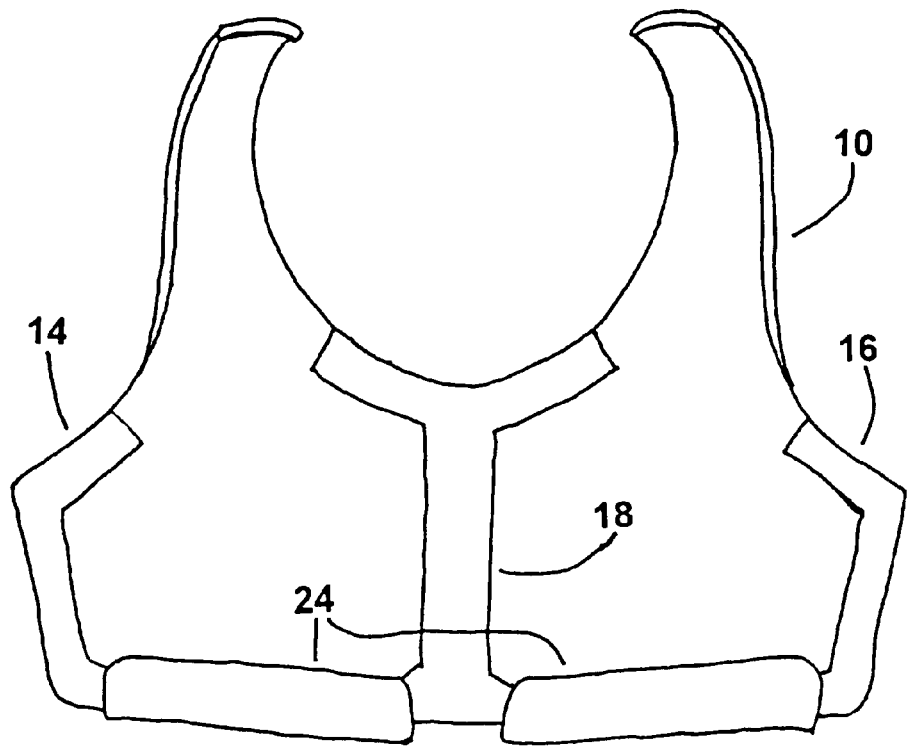
FIG. 4 shows a reverse view of the front portion of the shield.

On the reverse side of the frontal site shield 10 there are several sections of padding. A pad—left 14 is adhered to the left reverse of frontal site shield 10 with the use of adhesive. A pad—right 16 is adhered to the right reverse of frontal site shield 10 with the use of adhesive. A pad—center 18 is adhered to the center reverse of frontal site shield 10 with the use of adhesive. All three of the pads 14, 16, 18 are a made from a dense, firm closed-cell foam or other similar material. The purpose of the padding is to distribute the force of an impact away from the catheter site by maintaining an adequate void between the patient's skin, catheter, and the reverse side of frontal site shield 10 while cushioning any impact to the portions of the torso that touch the padding. FIG. 4 shows the location of these pads.

In order to hold frontal site shield 10 to the patient's torso, the device makes use of a backing material 12. This material connects frontal site shield 10 at the hook and loop enclosure 20, 22. The backing material is made from a flexible material that has the ability to stretch in a multi-directional manner. All hook or loop enclosures attach to backing material 12 by means of sewing or with an adhesive such as fabric glue. The backing material 12 can be made from fabric that is typically referred to as wetsuit neoprene. Although other materials with similar properties may be used, this material is superior in shape memory, strength, and comfort. The hook and loop enclosures 20, 22 have been made from a product commonly referred to as Velcro™.

On the reverse side of the frontal site shield 10 there are several sections of padding. A pad—left 14 is adhered to the left reverse of frontal site shield 10 with the use of adhesive. A pad—right 16 is adhered to the right reverse of frontal site shield 10 with the use of adhesive. A pad—center 18 is adhered to the center reverse of frontal site shield 10 with the use of adhesive. All three of the pads 14, 16, 18 are a made from a dense, firm closed-cell foam or other similar material. The purpose of the padding is to distribute the force of an impact away from the catheter site by maintaining an adequate void between the patient's skin, catheter, and the reverse side of frontal site shield 10 while cushioning any impact to the portions of the torso that touch the padding. FIG. 4 shows the location of these pads.

In order to hold frontal site shield 10 to the patient's torso, the device makes use of a backing material 12. This material connects frontal site shield 10 at the hook and loop enclosure 20, 22. The backing material is made from a flexible material that has the ability to stretch in a multi-directional manner. All hook or loop enclosures attach to backing material 12 by means of sewing or with an adhesive such as fabric glue. The backing material 12 can be made from fabric that is typically referred to as wetsuit neoprene. Although other materials with similar properties may be used, this material is superior in shape memory, strength, and comfort. The hook and loop enclosures 20, 22 have been made from a product commonly referred to as Velcro™.

Figure 7:
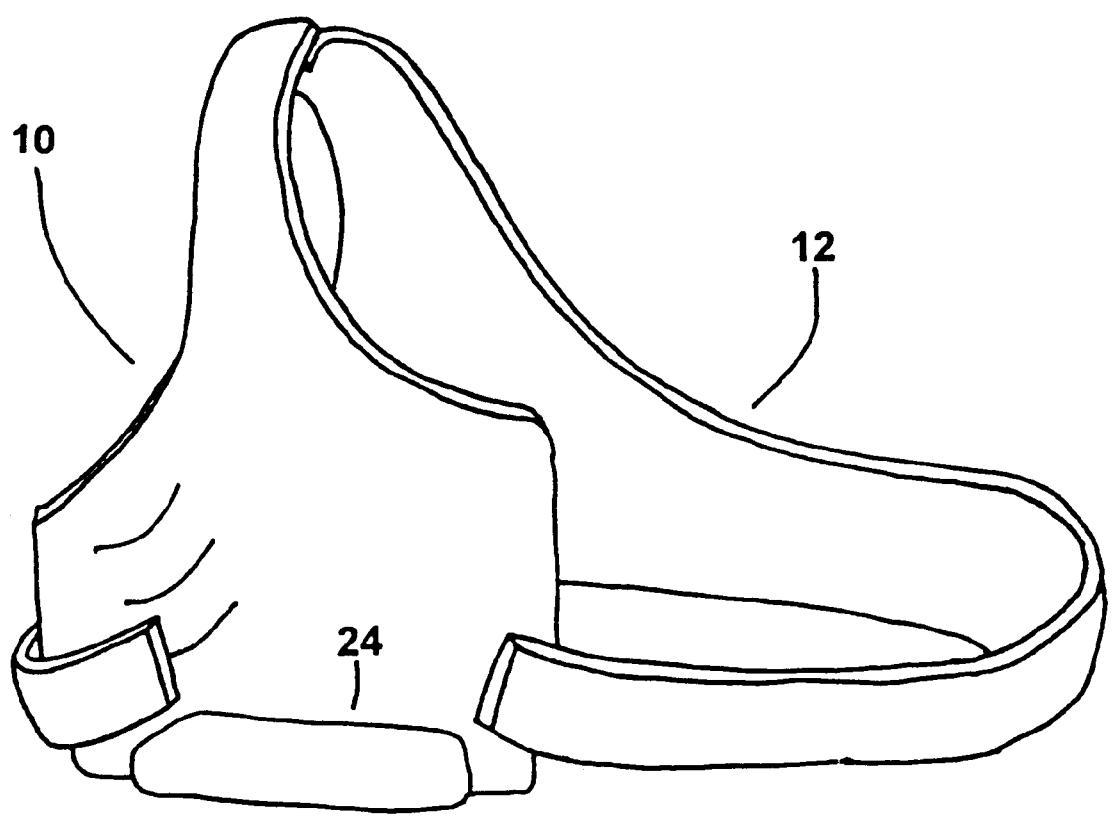
FIG. 7 shows a frontal view of an alternative embodiment of the device.

FIG. 7—Alternative Embodiment

As an alternative embodiment of this device, it is possible to create a device that covers only one portion of the torso, either the right or the left, depending upon which side of the patient the catheter or other medical device is implanted. FIG. 7 shows a right-side option of the device. A left-side option is also available, although not shown.

OPERATION OF INVENTION

Figure 5:
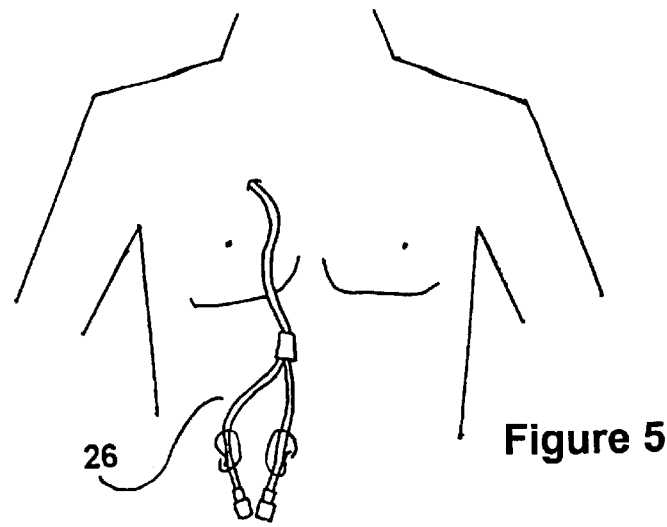
FIG. 5 shows a patient with a catheter surgically implanted. No device shown.
Figure 6:
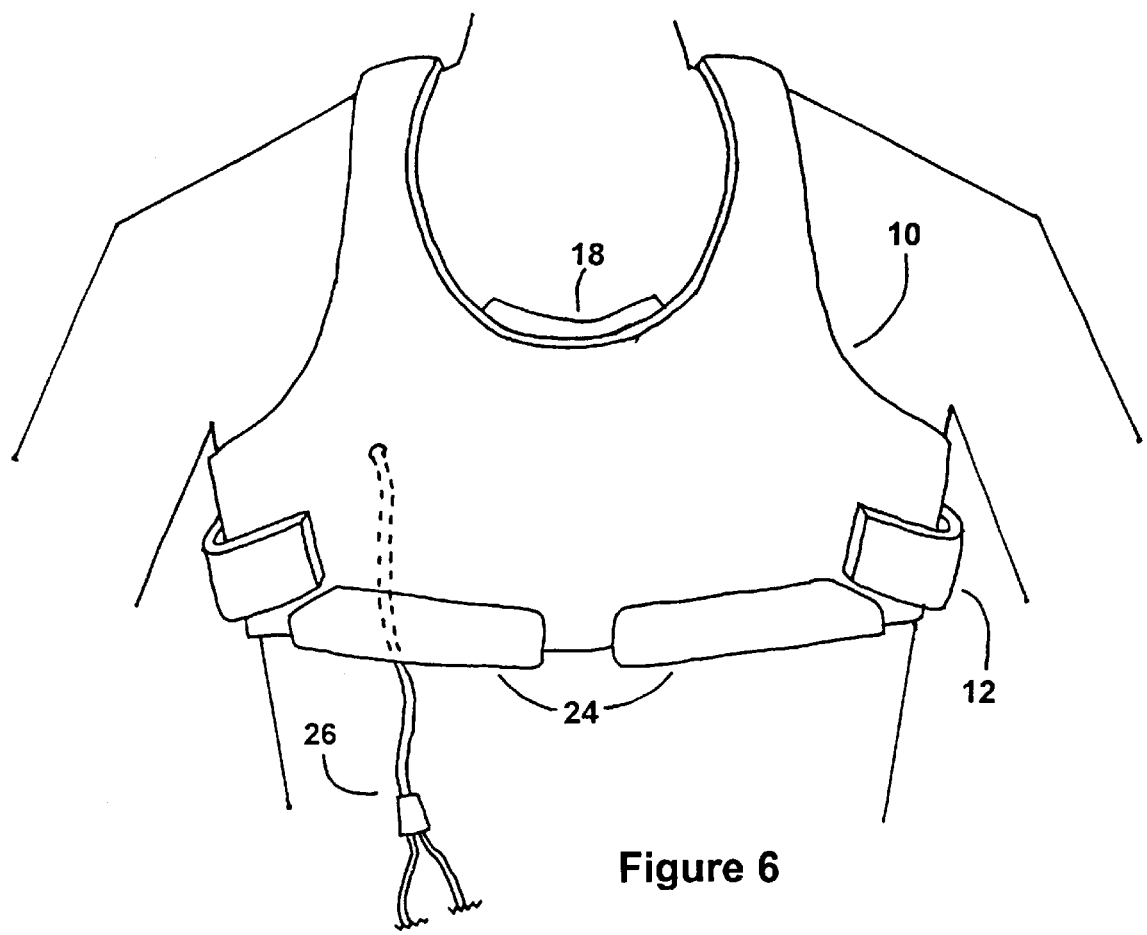
FIG. 6 shows a frontal view of a patient wearing the device.

The manner of using the protective shield is to begin as shown in FIG. 5 and position the shield onto the patient's torso and attaching as shown in FIG. 6. The operation of the invention is limited to simply attaching the device to the body.

A method to attach is to secure backing material 12 at the shoulder using enclosure—hook 20 on the right or the left side of frontal site shield 10 to the corresponding enclosure—loop 22. Place the device around the neck of the patient with one side attached at the shoulder. The patient continues by affixing the remaining shoulder by the same method.

The patient now affixes a side strap of backing material 12 around the torso to the front of the frontal site shield 10 by connecting enclosure—hook 20 to enclosure—loop 22. The patient completes the placement of the device by affixing the remaining strap around the torso and attaching to the front of frontal site shield 12 in the same manner as described above. The patient will stretch the backing material 12 in order to achieve a preferred fit.

Conclusions, Ramifications, and Scope

Accordingly, the reader will see that the protective shield will adequately protect the patient's site of an indwelling catheter or other medically implanted device. Furthermore, the shield has additional advantages in that it allows the production of the rigid frontal site shield to be made from a variety of materials that are conducive to the rigid, protective requirement;

it permits that the device may be sized to fit the wearer of an indwelling catheter or other medical device;

it permits the backing material may be produced from any desirable material;

it provides that the padding may be relocated or reshaped to accommodate other medical devices;

it permits that the device may be made integrally or separately as to accommodate and take advantage of manufacturing efficiencies or advances; and it provides protection of chest implanted medical devices.

Although the description above contains many particulars, these should not be construed as limiting the scope of the invention but as merely providing illustrations of some of the presently preferred embodiments of this invention.

Thus the scope of the invention should be determined by the appended claims and their legal equivalents, rather than by examples given.

I claim:

1. An article that protects patients with implanted Hickman-style catheter devices in or about the chest region of the body, comprising:

a rigid shield which covers the site of the implanted catheter and shaped to fit the chest region of the wearer;

a plurality of impact absorbing material affixed to said shield in order to surround the catheter site and create a void between said shield and the body wherein the catheter is positioned without contact to said shield nor said impact absorbing material;

a backing material comprised of a flexible fabric that allows for a consistent proper position, said plurality of impact absorbing material further comprises a piece of impact absorbing material attached at the center of said rigid shield, said piece of impact absorbing material having a vertical portion and two portions extending outwardly from the top of said vertical portion to provide a void between said rigid shield and the patient's body;

means for adjoining said backing material to said shield so as to retain securely the article in a proper position.

* * * * *